United States Patent [19]

Van Sorge

[11] 3,974,229

[45] Aug. 10, 1976

[54] PREPARATION OF ORTHO-ALKYLATED PHENOLS

[75] Inventor: Bernardus J. Van Sorge, Selkirk, N.Y.

[73] Assignee: General Electric Company, Pittsfield, Mass.

[22] Filed: Feb. 11, 1971

[21] Appl. No.: 114,698

Related U.S. Application Data

[63] Continuation-in-part of Ser. No. 846,973, Aug. 1, 1969, abandoned, which is a continuation-in-part of Ser. No. 717,919, April 1, 1968, abandoned.

[52] U.S. Cl. ............................ 260/621 R; 252/471; 260/620; 260/624 C
[51] Int. Cl.² ......................................... C07C 37/16
[58] Field of Search ............ 260/621 R, 624 C, 620

[56] References Cited
UNITED STATES PATENTS 3,446,856  5/1969  Hamilton ................... 260/621 R X

FOREIGN PATENTS OR APPLICATIONS 717,588  10/1954  United Kingdom............. 260/621 R Primary Examiner—Norman Morgenstern
Attorney, Agent, or Firm—William F. Mufatti; Edward A. Hedman

[57] ABSTRACT

There are provided alkylation catalysts comprising magnesium oxide mixed with and bonded by manganese oxides. These are used in processes for the vapor phase ortho-alkylation of phenols with an alcohol. The present catalysts are advantageous in that they provide a substantially increased total useful life, a reduced induction period for maximum reaction selectivity, elimination of catalyst losses in comparison with the powders or weakly sintered composites of the prior art and increased selectivity for ortho-substitution. Treatment of the new catalysts with methanol vapor before use enhances their activity in converting phenols to 2,6-xylenol and results in a significant increase in production rate.

15 Claims, No Drawings

PREPARATION OF ORTHO-ALKYLATED PHENOLS

CROSS-REFERENCE TO RELATED APPLICATIONS

This application is a continuation-in-part of copending U.S. patent application Ser. No. 846,973, filed Aug. 1, 1969, which in turn is a continuation-in-part of Ser. No. 717,919, filed April 1, 1968 both now abandoned.

This invention relates to the ortho-alkylation of phenols and more particularly, to the vapor phase ortho-alkylation of phenols by reaction of a non-ortho-alkylated phenol with an alcohol in the presence of a catalyst comprising magnesium oxide mixed with a manganese oxide.

BACKGROUND OF THE INVENTION

In commonly assigned Hamilton U.S. patent application Ser. No. 371,189, filed May 29, 1964, now U.S. Pat. No. 3,446,856, there is disclosed and claimed a method for methylating the ortho positions of phenol by the vapor phase reaction of a phenol with methanol in the presence of magnesium oxide as a catalyst at a catalyst bed temperature in the range of 475° to 600°C. Under the conditions described in the Hamilton patent, phenol is selectively ortho-methylated in yields of 95%. Thus, the reaction offers a means for economically converting phenol to ortho-cresol, a useful disinfectant and wood preservative and for converting both phenol and ortho-cresol to 2,6-xylenol, a monomer which can be polymerized to form poly(2,6-dimethyl-1,4-phenylene)oxide, a high performance thermoplastic material.

While the Hamilton patent provides an economic synthesis for both 2,6-xylenol and ortho-cresol from phenol, the service life of the magnesium oxide catalyst is relatively short due to the high temperature at which the reaction is required to take place, i.e., about 90 to 100 hours service life at the typical reaction temperature of about 530°C. Also, the magnesium oxide catalyst of the Hamilton patent is only moderately selective with respect to methanol, with methanol selectivity being in the range of about 40 to 50%. This means more than about two moles of methanol are required for each mole of methanol entering into the reaction with phenol. In addition, the use of unmodified magnesium oxide in powdered form or in the form of a weakly sintered composite results in a rather large induction period for maximum selectivity. The term "induction period" may be defined as the period from the time of starting the reaction to the time at which the catalyst reaches and maintains maximum ortho-alkylation selectivity. Finally, the use of magnesium oxide in powdered or sintered form provides various processing difficulties.

Many of the above-noted difficulties are overcome by the process of the said copending U.S. patent application Ser. No. 717,919, filed Apr. 1, 1968. Therein, a process is disclosed for the ortho-alkylation of phenol comprising the reaction of a phenol having at least one unsubstituted ortho position with an alcohol in the presence of a catalyst consisting of a mixture of magnesium oxide and manganese sulfate.

The catalyst of copending patent application Ser. No. 717,919 is prepared by pulverizing the magnesium oxide and wet-mixing the magnesium oxide with manganese sulfate and water or, alternatively, by impregnating the pulverized magnesium oxide with an aqueous solution of manganese sulfate. Preferably, the manganese sulfate constitutes from 2 to 10% of the catalyst on a dry solids basis. After mixing, it is preferred to mold the catalyst to a desired shape. It is disclosed that interaction between the manganese salt and the magnesium oxide upon contact with water from wet mixing or impregnation with aqueous solution is accompanied by the evolution of heat. Since the surface to weight ratio of the magnesium oxide is very high, for example, of the order of 180 square meters per gram, the heat brings about a noticeable increase in the mixture temperature under normal impregnating or mixing conditions. This appears to result in the formation of a lattice of enhanced catalytic activity containing the magnesium oxide and manganese sulfate.

With the catalyst of application Ser. No. 717,919, selectivity favoring ortho-methylation over meta- or para-methylation is the same as that of the Hamilton patent at temperatures as low as 440°C. It is advantageous to operate at temperatures as low as 440°C. instead of, for example, 530°C., because catalyst life is extended considerably before regeneration or other treatment is needed. Such catalysts have been operated without reduction in catalytic activity for periods in excess of 800 hours, in contrast to a maximum life of 90–100 hours for the Hamilton catalysts. In addition, the magnesium oxide-manganese sulfate catalyst is superior because of the increased strength imparted to the catalyst particles by the manganese oxide lattice formed by the reaction between manganese sulfate and magnesium oxide in the presence of water. Therefore, there is much less tendency for particles of catalyst to flake off in operation or from handling and the service life is thus extended with a minimum loss of catalyst.

Although the catalyst of the said copending application Ser. No. 717,919 provides the advantages noted above, there is observed an undesirable increase in the induction period required for maximum reaction selectivity. This means that about 24–100 hours is required to reach a molar phenol selectivity level of over 90%. During the induction period, a relatively large amount of undesired 2,4,6-mesitol is produced. It is believed that the presence of the sulfate ion in the catalyst is responsible for the longer induction period.

It has now been found that magnesium oxide mixed or bonded with manganese oxide or a mixture of manganese oxides has the advantages of the catalyst of the above-noted copending application and also, because sulfate is eliminated, has the further advantage of having a reduced induction period for maximum ortho-alkylation selectivity. Thus, the present invention contemplates an ortho-alkylation catalyst consisting of magnesium oxide mixed with manganese oxides, substantially free of sulfate, permitting the ortho-alkylation reaction to proceed with a high degree of both methanol and phenol selectivity and with a reduced induction period for maximum selectivity. Moreover, the new catalysts may be molded to any desired shape and will have strength properties sufficient to prevent particles of the the catalyst from breaking or flaking off in operation or handling, thus substantially extending the service life of the catalyst with a minimum of loss during operation. In addition the optimum reaction temperature may be reduced from 500°–540°C. for conventional catalysts down to 465°–485°C., thereby improving the overall economy of the process and increasing the catalyst life further.

It has also been discovered that if the catalysts according to this invention are treated with methanol vapor before use, there is an unexpected, significant increase in conversion of phenols to ortho-alkylated products. This in-situ activation provides an economical means of heating up a large commercial size reactor and results in a significant increase in production rate, of at least about 50% and more.

Accordingly, a primary object of the present invention is to provide an improved catalyst for the ortho-alkylation of a phenol with an alcohol in a highly selective manner and in high yield.

Another object of the invention is to provide a magnesium oxide catalyst having superior physical strength properties, which may be molded to any desired shape and which will have a service life of many hundreds of hours before needing regeneration or other treatment.

Still another object of the invention is to provide a process for formation of ortho-alklated phenols where the induction period required to reach maximum selectivity is low.

A further object of the invention is to provide an activated catalyst by exposure to methanol vapors.

DESCRIPTION OF THE INVENTION

These and other objects are secured according to this invention in providing a catalyst by mixing magnesium oxide wth manganese oxides, preferably in the form of finely divided powders. Preferably, the powders of the magnesium oxide and the manganese oxide are maintained below an average particle size of 500 microns in diameter. The percentage of manganese oxides in the blend is preferably maintained low and may be as low as 1% by weight on a dry solids basis or as high as 15% or more. The especially preferred range, however, varies from 2 to 10% by weight. After the powders are blended, water is added to the mixture in an amount sufficient to completely wet it so that the moist mixture may be molded to shape. Typically, one part by weight water is added for each part of the powder blend. The blend is then molded to shape under pressure, dried at about 200°F. and subsequently calcined at an elevated temperature. A calcination temperature of between 300° and 700°F. for a time up to about 3 hours is sufficient, but temperatures as high as 850°F. may be used. As water is evaporated from the catalyst, minute pores form and thereby expose the magnesium oxide increasing the catalyst activity. A surface area of at least 20, and preferably 120 to 200 square meters per gram of catalyst is desirable. The shape of the catalyst may be in the form of pellets, Rasching rings, cylinders, tablets or any other shape known to the art.

The magnesium oxide used as a catalyst in conjunction with the manganese oxides is a material having a very high surface to weight ratio. Magnesium oxide having the desired porosity may be prepared by thermally decomposing magnesium carbonate, basic magnesium carbonate or magnesium hydroxide as these materials may be converted to magnesium oxide without fusing or sintering.

The manganese oxides may be manganese oxide (MnO), dimanganese trioxide ($Mn_2O_3$), trimanganese tetroxide ($MN_3O_4$), manganese heptoxide ($Mn_2O_7$) as well as other complex oxides of manganese, and mixtures of such oxides. Especially preferred are dimanganese trioxide and trimanganese tetroxide. Manganese oxide may be obtained by precipitation from an aqueous solution of manganese sulfate by mixing with an alkali such as potassium hydroxide. However formed, best results are obtained if the manganese oxides powders are washed with distilled or slightly alkaline water until substantially free of ions, especially sulfate and potassium ions.

In a preferred feature, the catalyst prepared as described above is activated by exposing it to methanol vapor, e.g., by heating at a temperature of at least about 250°C., until activation is substantially complete. In one manner of proceeding, a catalyst according to this invention, e.g., magnesium oxide containing 2 or 5% of $Mn_2O_3$ is exposed to condensing methanol vapor for about 23 hours. The methanol can be vaporized in a separate, empty reactor at a temperature of about 250–300°C., then fed to the reactor containing the heated catalyst samples. The temperature of the catalyst can be raised to about 465°C. during 5 hours and maintained for another 16 hours. These times are illustrative, not critical — it is merely necessary to heat the catalyst with methanol vapor at a temperature above 250°–300°C. unitl activation of the catalyst is substantially complete.

According to this invention ortho-alkylated phenols are formed by a process which comprises vapor-phase reaction of an alkyl alcohol, e.g., a saturated aliphatic alcohol such as methyl, ethyl, propyl, isopropyl, butyl, isobutyl, tert.-butyl, amyl isoamyl, hexyl, heptyl, octyl, nonyl, decyl, undecyl, lauryl, cetyl, cyclohexyl, and the like, alcohols, and especially preferably an alcohol containing up to 6 carbon atoms and most preferably methanol, and a phenol having at least one unsubstituted ortho position in the presence of the catalyst of this invention at a temperature of at least 420°C., and preferably at a temperature varying between 460° and 500°C., and especially preferably at 465°–485°C. In general, the process conditions are similar to those disclosed in the above-noted Hamilton patent, but differ therefrom primarily in the substitution of the catalyst of this invention and by use of a lower reaction temperature.

While the invention has been described as applying specifically to phenols and ortho-cresol, it may be applied in general to any phenol having an ortho-hydrogen. For example, it also may be used with ortho-phenyl phenol, ortho-ethyl phenol, and phenols in which there are alkyl and aryl groups in the meta- and para-positions. These phenols may be represented by the formula:

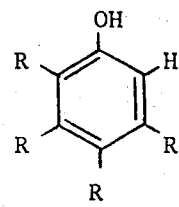

where each R is a monovalent substituent selected from the group consisting of hydrogen, alkyl, e.g., $C_1$–$C_{12}$ alkyl, phenyl and alkyl-substituted phenyl, e.g., $C_1$–$C_{12}$ alkyl-substituted phenyl.

In carrying out the alkylation in accordance with this invention, any one or a mixture of phenols having an ortho-hydrogen may be vaporized and passed through a reactor heated to a suitable temperature, e.g., at least 200°C., and preferably at least 420°C., containing the magnesium oxide-manganese oxides catalyst of the invention. In order to obtain the maximum yield of ortho-alkylated products, at least one mole of the alkyl alcohol and preferably from 1 to 3 moles of the alcohol are used for each ortho position on the phenol to be alkylated. For example, if phenol, which has two-ortho hydrogens per molecule, is to be methylated to produce a maximum yield of 2,6-xylenol, it is desirable to use two to six moles of methanol for each mole of phenol with higher yields being obtained with higher ratios of methanol to phenol.

The vapors issuing from the reactor are condensed and the product separated by conventional methods such as crystallization, distillation, etc. The reaction proceeds at atmospheric pressure, but it is obvious that pressures above or below may be used.

As will be apparent to those skilled in the art, the process can be carried out under a variety of reaction conditions. These conditions are temperature, pressure, flow rate of reactants, vapor space velocity of the reactants over the catalyst, contact time of the reactants with the catalyst, length of the catalyst bed, specific activity of the particular catalyst, etc. The effects of these reaction variables are those to be expected from a consideration of the technical aspects of the reaction involved. For example, the reaction of alcohol with the phenol compound to produce the desired ortho-alkylated products proceeds faster as the catalyst bed temperature is increased provided that the temperature is not so high that secondary reactions such as decomposition of the reactants or products occur to decrease the yield of desired product. Such secondary reactions do not occur to any appreciable extent in this reaction up to a temperature of about 500°C. Above 500°C., decomposition of the reactants and product becomes a problem because it deposits carbon on the catalyst, decreasing its activity. In contrast to prior art catalysts, in the range of from 275° to 500°C. when using a high proportion of methanol to phenol, i.e., 2–3 times the amount of methanol required to methylate each ortho-position of the phenol, the tendency to decompose methanol to gaseous products is decreased. Below a temperature of 200°C., the reaction of methanol with the phenol is so slow that the yield of product per hour per volume of catalyst is so low as to make the reaction uneconomical to carry out, regardless of the reaction conditions.

In accordance with well known techniques to compensate for lower rates of reaction, if, for example, less reactive phenolic compounds or alkanols are used, a longer contact time of the reactants with the catalyst can be used. This may be done by changing any one or several of the variables which decrease the vapor space velocity of the reactants over the catalyst, thus increasing the contact time. Examples of this are increasing the amounts of catalyst, decreasing the flow rate of reactants, increasing the pressure in the reactor, etc. At the lower flow rates, there is some tendency for the selectively to decrease because the longer contact time does permit any product which has been completely substituted in the two ortho-positions in the initial part of the reaction to have time to react further to produce some para-substituted product. This loss in selectivity can be compensated by increasing the space velocity but not the flow rate of reactants by using an inert diluent for the reactants; for example, an inert gas, i.e., nitrogen, argon, etc., or an inert vapor, i.e., benzene, toluene, etc., or by using a lower pressure in the reactor.

If it is desired to use pressure, the flow rate of the reactants can be increased to give an equal contact time. It, of course, will be recognized that it is possible to have a flow rate of reactants so great, either with or without pressure, that the effective contact time is reduced to an economically unsatisfactory level.

Generally, reaction conditions are chosen so as to minimize the amount of unreacted feed materials which must be recovered and reused. However, reaction conditions which on the face might appear undesirable from an over-all yield point of view may be desirable from an economic point of view because of the very high degree of selectivity of the reaction under such conditions to give exclusively only ortho-alkylated products. On the other hand, reaction conditions can also be adjusted to give high over-all yields in terms of pounds of ortho-alkylated product per hour per volume of catalyst when a very small yield of para-substituted product can be tolerated.

It will also be recognized that, because of differences in the specific activities of the catalysts, each particular catalyst will have different optimum reaction conditions than another catalyst. The more reactive the catalyst, the shorter the contact time needs to be to give the same degree of conversion to ortho-alkylated products. Therefore, a higher space velocity or a lower temperature may be used with a more reactive catalyst. It has been found that a catalyst which has not been used in the reaction, or has been regenerated, has an induction period during which time the selectivity of the catalyst increases until it reaches a maximum which it maintains for a long period of time.

DESCRIPTION OF THE PREFERRED EMBODIMENTS

In order that those skilled in the art may better understand the invention, the following examples are given by way of illustration and not by way of limitation.

In the examples, the reactor consists of a reservoir containing a solution of alcohol and phenol compound, connected to a metering pump which feeds the reactants through a ¼ inch stainless steel tube into a vertical vaporizer made from a 12-inch long piece of 1 inch O.D. × 0.8 inch I.D. stainless steel tubing. The vaporizer is partially immersed in a bath of fused salt to a depth of about 6 inches. The vapors from the vaporizer are fed to an 0.8 inch I.D. stainless steel tube reactor through a 1 inch length of 0.25 inch I.D. stainless steel pipe located 5.50 inches above the bottom of the vaporizer and connected to the reactor 13 inches from its bottom. The reactor is 24 inches long and is immersed in the fused salt bath to a depth of 14 inches. Since the inlet tube of the reactor coming from the vaporizer also passes through the fused salt bath, it serves as a preheater for the vapor issuing from the vaporizer to bring the vapor up to the temperature of the reactor. The reactor is equipped with a thermowell made from ⅛ inch stainless steel tubing concentrically located in the reactor and extending downwards into the catalyst bed to a depth of 1 to 6 inches. Thus the catalyst bed temperature can be measured throughout a large section of the tube. The reactor tube is filled with about 20 ml. of glass beads and then 100 ml. of catalyst is introduced which fills the tube to a depth of 14 inches. The reactant vapors are fed to the top of the catalyst bed and product vapors leave the bottom of the reactor through a ⅜ inch O.D. stainless steel outlet tube. The product vapors are led to a water-cooled condenser and receiver.

EXAMPLE 1

A catalyst is prepared by blending 200 grams of commercial magnesium oxide with about 6 grams of a mixture of manganese oxides precipitated from an aqueous solution of manganese sulfate mixed with an aqueous solution of potassium hydroxide and washed with water until sulfate ion free. The mixture of magnesium oxide and manganese oxide is mixed with about an equal amount of water and the so-formed blend is molded into cylindrically shaped pellets having a diameter and length of 3/16 inches. The catalyst is dried at 200°F. and calcined by heating to about 450°F. for about 3 hours. The catalyst is then placed in a reactor which is maintained at 460°C. The feed composition is vaporized and the vapors are passed through the catalyst chamber. The conditions and results are summarized in Table I:

TABLE I

| Feed Composition | Run 1 |
| --- | --- |
| Molar Ratio Methanol to Phenol | 6:1 |
| Wt. % Water in Feed | 6 |
| Operating Conditions | |
| Temperature (°C.) | 460 |
| LHSV (hr$^{-1}$)* | 2.03 |
| Pressure (psig) | 0 |
| Phenolic Distribution (wt.%) | |
| o-cresol | 10.1 |
| 2,6-xylenol | 65.4 |
| 2,4,6-mesitol | 1.1 |
| Phenol | 23.4 |

*LHSV is the liquid hourly space velocity and defines the volume of liquid per volume of catalyst per hour.

From the above table, it can be seen that the alkylation takes place primarily in the ortho position. The ortho-cresol formed in the reaction and unreacted phenol may be recycled if desired. By increasing the liquid hourly space velocity, the ratio of ortho-cresol to 2,6-xylenol may be substantially increased. For example, using substantially the same reaction conditions, an increase in the space velocity to about 3.50 hrs$^{-1}$ results in a phenolic distribution comprising about 45% unreacted phenol, 38% ortho-cresol, 16% 2,6-xylenol and less than 1% 2,4,6-mesitol.

EXAMPLE 2

The procedure of Example 1 is repeated. In Run 2a, the catalyst used is substantially the same as that of Example 1. In Run 2b, the catalyst is prepared by pelletizing and calcining substantially pure powdered magnesium oxide at a temperature of about 500°F. The conditions and results are as indicated in Table II:

TABLE II

| Feed Composition | Run 2a | Run 2b |
| --- | --- | --- |
| Molar ratio Methanol to Phenol | 6:1 | 6:1 |
| Wt. % water in feed | 10 | 12.4 |
| Operating Conditions | | |
| Temperature (°C.) | 489 | 504 |
| LHSV (hr.$^{-1}$) | 1.83 | 1.65 |
| Pressure (psig) | 0 | 0 |
| Results | | |
| Induction Period (hrs.) | 8 | 23.5 |
| Molar Phenol Selectivity[1] | 93.7 | 89.5 |
| Molar Methanol Selectivity[2] | 72.5 | 59.5 |
| Production Rate | 19.3 | 14.0 |

TABLE II-continued (lbs. 2,6-xylenol/hr./ft. catalyst)

[1]The molar phenol selectivity is defined as the ratio of phenol converted to 2,6-xylenol to phenol converted to 2,6-xylenol and by-products multiplied by 100. The amount of phenol converted to ortho-cresol is not included in the definition as it is recycled in the feed stream if desired.
[2]The molar methanol selectivity is defined as the ratio of methanol reacted to form 2,6-xylenol to the methanol reacted to form 2,6-xylenol and by-products multiplied by 100. The amount of methanol converted to ortho-cresol is not included in the definition as it is recycled in the feed stream if desired.

The life of the catalyst of Run 2a is found to be in excess of 1000 hours compared to a life of approximately 75 hours for the conventional catalyst of Run 2b. From Table II, it can also be seen that the induction period for the reaction using a catalyst according to this invention is shorter than for the prior art magnesium oxide catalyst. Moreover, methanol selectivity is substantially improved. The Crushing Strength of the catalyst of Run 2a is found to be approximately 56 pounds. This compares to a Crushing Strength of approximately 5 pounds for the conventional catalyst of Run 2b, both tests being run on the sides of cylindrical pellets.

EXAMPLE 3

A catalyst is prepared by dry-mixing magnesium oxide powder with 5 wt.% of di-manganese-trioxide ($Mn_2O_3$), followed by wetting, pelletizing and drying as described in Example 1. After calcining for 3 hours at 600°F., the crushing strength is 31 lbs. as opposed to about 5 lbs. for a conventional magnesium oxide catalyst.

The catalyst is placed in a reactor which is maintained at 480°C. The feed composition is vaporized and the vapors are passed through the catalyst chamber (Run 3a). For comparison purposes a conventional magnesium oxide catalyst is used (Run 3b). The conditions and results are summarized in Table III.

TABLE III

| Feed Composition | Run 3a | Run 3b |
| --- | --- | --- |
| Molar Ratio Methanol to Phenol | 6:1 | 5:1 |
| Wt. % Water in Feed | 6 | 12.4 |
| Operating Conditions | | |
| Temperature (°C.) | 480 | 539 |
| LHSV (hr$^{-1}$) | 2.5 | 0.55 |
| Pressure (psig) | 0 | 0 |
| Results | | |
| Elapsed Run Time (hrs) | 200 | 72 |
| Product Rate | 25 | 4 |
| Phenolics distribution (wt.%) | | |
| o-cresol | 18.6 | 46.3 |
| 2,6-xylenol | 50.2 | 40.0 |
| 2,4,6-xylenol | 2.9 | 0.7 |
| phenol | 28.1 | 13 |
| Total duration of Run (hrs) | 400 | 200 |

It is seen that the operating temperature with a catalyst according to this invention (Run 3a) can be maintained at about 480°C. as opposed to 539°C. for the conventional, commercially available magnesium oxide catalyst (Run 3b). It is also found that with the catalyst of Run 3a, the molar phenol selectivity reaches a level of over 90% in less than 8 hours, as opposed to about 24–100 hours for the conventional catalyst of Run 3b. The process using the catalyst according to this invention (Run 3a), therefore, is characterized by the surprising absence of any lasting induction period and quickly reaches a high selectivity for ortho-alkylation.

EXAMPLE 4

The procedure of Example 3 is repeated substituting for the di-manganese trioxide, an equal weight of tri-manganese tetroxide ($Mn_3O_4$). Substantially the same results are obtained.

EXAMPLE 5

Two catalysts are prepared by the procedure of Example 3 containing, respectively, 5 wt.% (Run 5a) and 2 wt.% (Run 5c) of di-manganese trioxide, $Mn_2O_3$. Approximately 100 ml. each are exposed to methanol which has been vaporized in separate, empty reactors, which are located in a salt bath at a temperature of about 300°C., then led to the reactors containing the catalyst samples. After 23 hours, these two reactors, together with a third one which serves as a control and contains approximately 100 ml. of the 5% $Mn_2O_3$ catalyst (Run 5b), are placed in the salt bath at 300°C. and the methanol flow through the methanol vapor treated catalyst is continued. Nitrogen is passed through the control at 2 cubic feet per hour. The temperature in the salt bath is increased to 465°C. during 5 hours, and these conditions are maintained for an additional 16 hours. For comparison purposes, a 2% $Mn_2O_3$ control is also used (Run 5d). The conditions and results are summarized for three different elapsed times (measured from the beginning of the runs) in Table IV:

TABLE IV

| Run | Catalyst | Hrs. into Run | Temp., °C. | Flow ml./hr. | % 2,6-xylenol in phenolics of Reactor effluent | Production rate |
|---|---|---|---|---|---|---|
| 5a | 5% | 2 | 463 | 253 | 36.8 | 19.9 |
| 5b | 5% control | 2 | 463 | 234 | 22.6 | 10.5 |
| 5c | 2% | 2 | 469 | 270 | 37.6 | 21.5 |
| 5d | 2% control | 2 | 469 | 220 | 31.3 | 14.2 |
| 5a | 5% | 73 | 473 | 268 | 60.6 | 34.6 |
| 5b | 5% control | 73 | 473 | 270 | 31 | 16.5 |
| 5c | 2% | 73 | 473 | 268 | 51.7 | 29.1 |
| 5d | 2% control | 67 | 486 | 250 | 48.3 | 25.3 |
| 5a | 5% | 172 | 478 | 254 | 64.2 | 34.7 |
| 5b | 5% control | 172 | 478 | 255 | 35.3 | 17.9 |
| 5c | 2% | 174 | 478 | 254 | 43.8 | 22.8 |
| 5d | 2% control | 170 | 483 | 240 | 33.9 | 16.4 |

It is noteworthy that the 2% control (Run 5d) had a higher optimum operating temperature and a still lower production rate than the same catalyst preactivated with methanol vapor (Run 5c).

The overall results in Table IV demonstrate that there is an unexpected, significant increase in the conversion of phenol to 2,6-xylenol following treatment of the catalyst according to this invention with methanol vapor.

EXAMPLE 6

A catalyst comprising magnesium oxide and 5% by weight of dimanganese trioxide ($Mn_2O_3$) is prepared by the procedure of Example 3. It is divided into three portions, one is treated with methanol vapor, one is treated with nitrogen gas and the third is heated in the air at 455°C. (850°F.) for 3 hours. The start-up conditions were as follows:

| Steps | nitrogen start-up | methanol start-up |
|---|---|---|
| (1) | insert in salt bath at 250°C. | same |
| (2) | bleed with $N_2$ at 2 SCFH for ½ hr. | same |
| (3) | continue $N_2$ flow | start McOH flow at 250 ml/hr. |
| (4) | raise temp. to 370°C. in 3 hrs. | same |
| (5) | hold temp. at 370°C. for 36 hrs. | same |
| (6) | increase temp. to 465°C. in increments of 20°C./hr. | same |
| (7) | hold at 465°C. for 16 hours. | same |
| (8) | same | bleed with $N_2$ for ½hr. |
| (9) | remove from salt bath | same |

SCFH means standard cubic feet per hour

The physical properties are measured and summarized in Table V:

TABLE V

| | $N_2$ Start-up | McOH Start-up | Catalyst heated at 455°C. |
|---|---|---|---|
| Average crush strength (pounds) | 4.8 | 7.9 | 6.4 |
| Total volatiles, % at 1750°F. | 3.83 | 8.75 | 4.22 |
| Chemical analysis | | | |
| Wt.% Carbon | 0.34 | 1.20 | 0 |
| Wt.% manganese, as $Mn_2O_3$ | 4.77 | 5.40 | 4.80 |
| Surface area, m.²/g. | 106 | 240 | 140 |
| Pore volume, cc./g. | 0.43 | 0.45 | 0.44 |
| Pore diameter, A | 163 | 74 | 125 |

All three catalysts are included within the scope of this invention. The "Catalyst with MeOH start-up" is a preferred embodiment because such catalysts are more active than the catalyst without (as is shown by the comparative results in Example 5).

As is seen by the data in Table V, the methanol vapor treated catalyst also has a higher crush strength than the nitrogen-treated or heat sintered embodiments.

Furthermore, although the mechanism by which the changes in physical properties have been induced is not clearly understood, a surprisingly large increase, of about 70%, in surface area is observed in the methanol treated sample. On the other hand, substitution of nitrogen for methanol causes a decrease of about 24% in surface area.

Although the pore volumes remain about constant, the average pore diameter, which is calculated by the formula:

$$\overline{PD} = \frac{4 \times \text{pore volume} \times 10^4}{\text{surface area}}$$

is smaller after the methanol treatment and larger after the nitrogen treatment.

EXAMPLE 7

The procedure of Example 1 is repeated, substituting for the methanol stoichiometrical amounts of the following alkanols: ethyl, propyl, n-butyl, isopropyl, isobutyl, tertiary butyl, n-amyl and n-hexyl. There are obtained, respectively, phenols, mono- and di-ortho-substituted with ethyl, propyl, n-butyl, isopropyl, isobutyl, tertiary butyl, n-amyl and n-hexyl groups.

EXAMPLE 8

The procedure of Example 1 is repeated substituting for the phenol, stoichiometrical amounts of the following phenolic compounds with at least one ortho-hydrogen:
o-cresol;
m-cresol;
p-cresol;
3,5-xylenol; and
2-phenylphenol The predominating products are, respectively:
2,6-xylenol;
2,3,6-trimethylphenol;
2,4,6-trimethylphenol;
2,3,4,6-tetramethylphenol; and
2-methyl-6-phenylphenol.

Similarly, after substituting for phenol the following phenolic compounds:
2,3-xylenol;
2,4-xylenol;
2,5-xylenol;
2,3,4-trimethylphenol;
2,3,5-trimethylphenol;
3,4,5-trimethylphenol;
2,3,4,5-tetramethylphenol;
4-phenylphenol;
2-tolylphenol;
2,4-diphenylphenol;
2,3-diphenylphenol;
2-xylylphenol;
2-mesitylphenol;
2-durylphenol;
4-methyl-2-phenylphenol;
2-tolyl-4-phenylphenol;
2-phenyl-4-tolylphenol; and
3-methyl-5-phenylphenol,
in the procedure of Example 1 there are obtained the corresponding mono-ortho-methylated and di-ortho-methylated phenols, depending on whether one or two of the ortho-positions is unsubstituted in the starting material.

Although the above examples have shown various modifications and variations of the present invention, other modifications and variations are possible in light of the above teachings. It is therefore to be understood that changes may be made in the particular embodiments of the invention described which are within the full intended scope of the invention as defined by the appended claims.

I claim:
1. In a process for alkylating a phenol in the ortho position which comprises the vapor phase reaction in the presence of an alkylation catalyst of an alkyl alcohol and a phenol compound having the general formula:

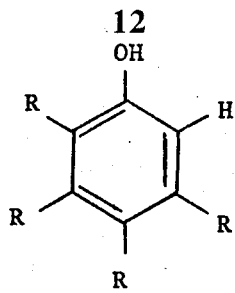

where R is a monovalent substituent from the group consisting of hydrogen, alkyl, phenyl and alkyl substituted phenyl; the improvement comprising conducting the reaction in the presence of a catalyst comprising magnesium oxide bonded with from 1–15% by weight of manganese oxides.

2. The process of claim 1 wherein said alcohol is methyl alcohol.

3. The process of claim 2 wherein the catalyst is maintained at a temperature of at least 420°C.

4. The process of claim 2 wherein each R in said phenol compound is hydrogen.

5. The process of claim 2 wherein said phenol compound is ortho-cresol.

6. The process of claim 2 wherein said phenol compound is a mixture of phenol and ortho-cresol.

7. The process of claim 1 wherein said manganese oxides are selected from the group consisting of manganese oxide, dimanganese trioxide, trimanganese tetroxide, manganese heptoxide and mixtures thereof.

8. The process of claim 1 wherein the manganese oxide binder is substantially free of sulfate ions and is formed by precipitation from an aqueous solution of manganese sulfate by contact with an alkali.

9. The process of claim 1 wherein the manganese oxides comprise from 1 to 15% by weight of the total catalyst.

10. The process of claim 1 wherein the manganese oxides comprise from 2 to 10% by weight of the total catalyst.

11. The process of claim 1 including the step of enhancing the activity of the catalyst by exposing it to methanol vapor before conducting the alkylation reaction.

12. The process of claim 11 wherein the catalyst is exposed to methanol vapor at a temperature of at least about 250°C. until activation of the catalyst is substantially complete.

13. In a process for alkylating phenol in the ortho position to form 2,6-xylenol which comprises the vapor phase reaction in the presence of an alkylation catalyst of an alkyl alcohol and phenol; the improvement comprising conducting the reaction in the presence of a catalyst comprising magnesium oxide bonded with from 1–15% by weight of manganese oxides.

14. In a process for alkylating a phenol in the ortho position which comprises the vapor phase reaction in the presence of an alkylation catalyst of an alkyl alcohol and a phenol compound having the general formula:

13

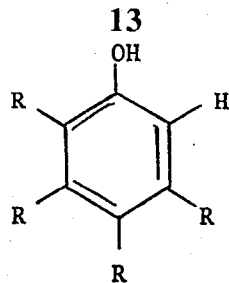

where R is a monovalent substituent from the group consisting of hydrogen, alkyl, phenyl and alkyl substituted phenyl; the improvement comprising conducting the reaction in the presence of a methanol vapor activated catalyst which comprises magnesium oxide bonded with from 1–15% by weight of manganese oxides.

15. In a process for alkylating a phenol in the ortho position which comprises the vapor phase reaction in the presence of an alkylation catalyst of an alkyl alcohol and a phenol compound having the general formula:

14

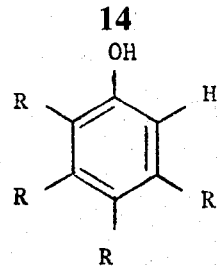

wherein R is a monovalent substituent from the group consisting of hydrogen, alkyl, phenyl and alkyl substituted phenyl; the improvement which comprises conducting the reaction in the presence of a catalyst prepared by blending a mixture of magnesium oxide with from 1–15% by weight of manganese oxide with about an equal amount of water, molding the blend to shape, and heating at a calcination temperature of from 300–850°.

* * * * *